United States Patent
Tsuji et al.

(10) Patent No.: US 10,024,843 B2
(45) Date of Patent: Jul. 17, 2018

(54) URINE SAMPLE ANALYZER, URINE SAMPLE DISPENSING METHOD AND URINE SAMPLE ANALYZING METHOD

(71) Applicant: Sysmex Corporation, Kobe-shi, Hyogo (JP)

(72) Inventors: Kentaro Tsuji, Kobe (JP); Yuta Okamura, Kobe (JP); Go Senda, Kobe (JP)

(73) Assignee: SYSMEX CORPORATION, Hyogo (JP)

(*) Notice: Subject to any disclaimer, the term of this patent is extended or adjusted under 35 U.S.C. 154(b) by 232 days.

(21) Appl. No.: 15/079,885

(22) Filed: Mar. 24, 2016

(65) Prior Publication Data

US 2016/0290990 A1    Oct. 6, 2016

(30) Foreign Application Priority Data

Mar. 31, 2015    (JP) .................. 2015-072225

(51) Int. Cl.

| | |
|---|---|
| *G01N 35/10* | (2006.01) |
| *G01N 33/493* | (2006.01) |
| *A61B 10/00* | (2006.01) |
| *B01L 3/00* | (2006.01) |
| *G01N 1/14* | (2006.01) |
| *G01N 1/31* | (2006.01) |

(52) U.S. Cl.
CPC ......... *G01N 33/493* (2013.01); *A61B 10/007* (2013.01); *B01L 3/52* (2013.01); *B01L 3/567* (2013.01); *G01N 1/14* (2013.01); *G01N 35/1004* (2013.01); *G01N 35/1009* (2013.01); *B01L 2200/141* (2013.01); *B01L 2300/0636* (2013.01); *B01L 2300/0681* (2013.01); *B01L 2400/049* (2013.01); *B01L 2400/06* (2013.01); *G01N 1/31* (2013.01); *G01N 2035/106* (2013.01); *G01N 2035/1053* (2013.01)

(58) Field of Classification Search
CPC .................................. G01N 35/10
See application file for complete search history.

(56) References Cited

U.S. PATENT DOCUMENTS

2015/0000428 A1    1/2015 Fukuda et al.

FOREIGN PATENT DOCUMENTS

JP    2015-10894 A    1/2015

*Primary Examiner* — Jyoti Nagpaul
(74) *Attorney, Agent, or Firm* — Brinks Gilson & Lione

(57) ABSTRACT

Disclosed is a urine sample dispensing method. The method comprises: (i) suctioning a urine sample using a nozzle; (ii) flowing the urine sample suctioned by the nozzle through a filter for capturing foreign matter, the filter being provided in a flow path connected to the nozzle; and (iii) changing a flow course of the urine sample or a position of the filter so that the filter is not positioned on the flow course of the urine sample, when the urine sample that has passed through the filter is discharged from the nozzle.

13 Claims, 18 Drawing Sheets

URINE SAMPLE ANALYZER, URINE SAMPLE DISPENSING METHOD AND URINE SAMPLE ANALYZING METHOD

RELATED APPLICATIONS

This application claims priority from prior Japanese Patent Application No. 2015-072225, filed on Mar. 31, 2015, entitled "URINE SAMPLE ANALYZER AND URINE SAMPLE DISPENSING METHOD", the entire contents of which are incorporated herein by reference.

BACKGROUND OF THE INVENTION

1. Field of the Invention

The invention relates to a urine sample analyzer, a urine sample dispensing method and a urine sample analyzing method.

2. Description of the Related Art

Japanese Patent Application Publication No. 2015-10894 discloses a device which performs processing of a sample suctioned from a container. The device may suction foreign matter such as debris fragments, pubic hair and the like, and has a filter to capture the foreign matter in suctioned urine samples.

Although the filter is constructed so that the captured foreign matter does not simply come off when the filter for removing foreign matter is provided, there is concern that the foreign matter captured by the filter will be discharged from the nozzle together with the urine sample when the urine sample is discharged from the nozzle.

SUMMARY OF THE INVENTION

The scope of the present invention is defined solely by the appended claims, and is not affected to any degree by the statements within this summary.

An aspect of the invention relates to a urine sample analyzer. The analyzer comprises: a nozzle which suctions and discharges a urine sample; a pressure source which generates pressures to suction and discharge the urine sample; a first flow path from the nozzle to the pressure source; a second flow path which branches from the first flow path at a first position of the first flow path, and which conjoins with the first flow path at a second position on the pressure source side of the first position; a filter for capturing foreign matter, which is placed in the first flow path between the first position and the second position; valves which control a flow of fluid in a flow path circuit that includes the first flow path and the second flow path; a controller which controls the valves so that the urine sample suctioned by the nozzle passes through the filter, and the urine sample that has passed through the filter bypasses the filter by passing through the second flow path and is discharged from the nozzle; a detector which detects information of material components in the urine sample discharged by the nozzle; and an analyzing part which analyzes the information of the material components detected by the detector.

Another aspect of the invention relates to a urine sample dispensing method. The method comprises: (i) suctioning a urine sample using a nozzle; (ii) flowing the urine sample suctioned by the nozzle through a filter for capturing foreign matter, the filter being provided in a flow path connected to the nozzle; and (iii) changing a flow course of the urine sample or a position of the filter so that the filter is not positioned on the flow course of the urine sample, when the urine sample that has passed through the filter is discharged from the nozzle.

Another aspect of the invention relates to a urine sample analyzing method comprising: (i) suctioning a urine sample using a nozzle; (ii) flowing the urine sample suctioned by the nozzle through a filter for capturing foreign matter, the filter being provided in a flow path connected to the nozzle; and (iii) changing a flow course of the urine sample or a position of the filter so that the filter is not positioned on the flow course of the urine sample, when the urine sample that has passed through the filter is discharged from the nozzle; and (iv) analyzing material components in the urine sample discharged from the nozzle.

DETAILED DESCRIPTION OF THE PREFERRED EMBODIMENTS

Hereinafter, preferred embodiments of the present invention will be described with reference to the drawings.

1. Structure of the Sample Analyzer

Figure 1:
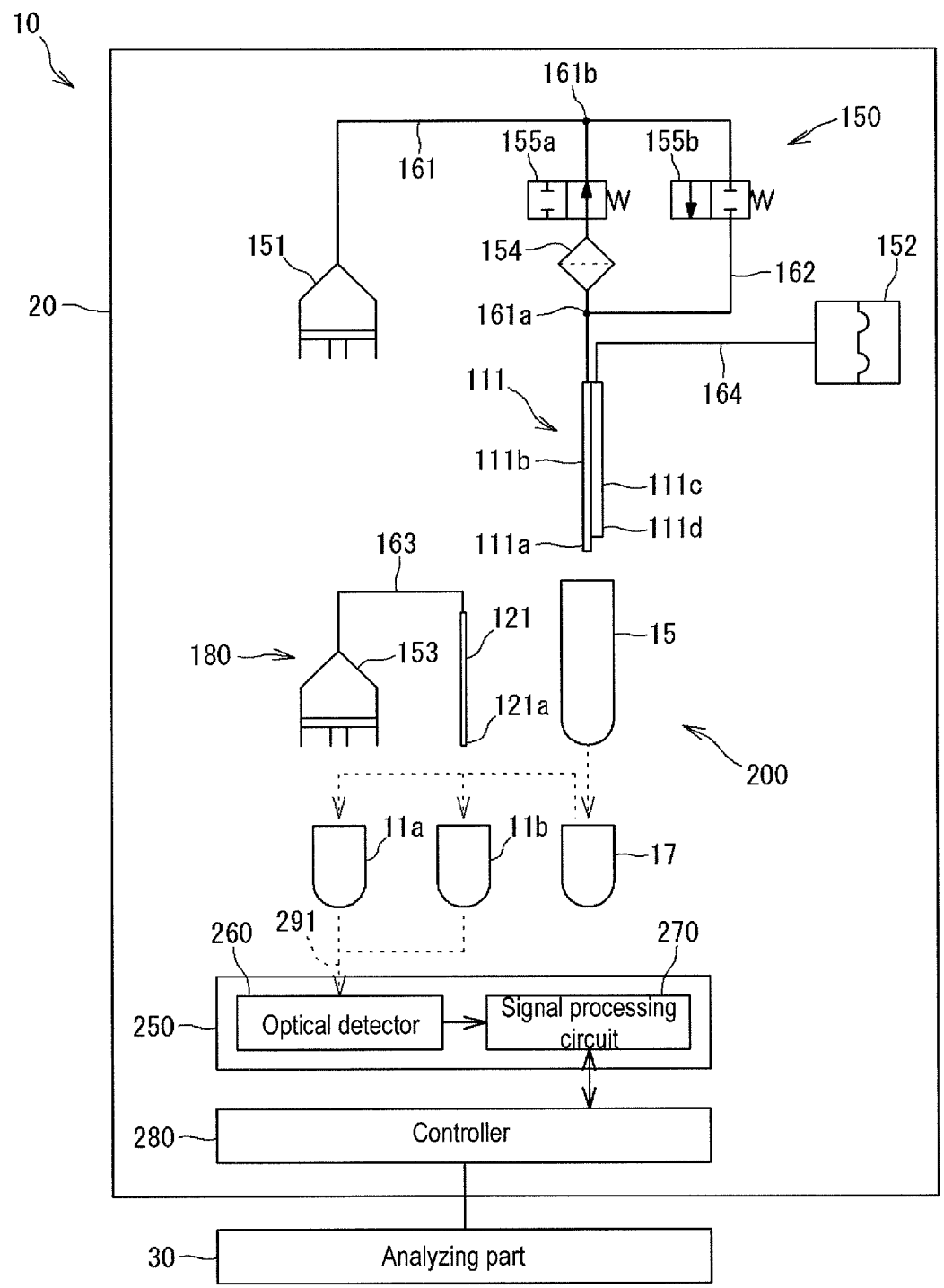
FIG. 1 is a structural view of the sample analyzer.

The urine sample analyzer shown in FIG. 1 analyzes urine sample. The sample analyzer 10 includes a measuring unit 20 which measures urine samples, and an analyzing part 30 which analyzes the output of the measuring unit 20. The measuring unit 20 includes a dispensing part 200, detecting part 250, and controller 280.

The dispensing part 200 suctions the urine sample from a sample container 15, and dispenses the urine sample in the sample container 15 into processing chambers 11a and 11b. The detecting part 250 detects information of the components in the sample. The detecting part 250 includes an optical detector 260 and a signal processing circuit 270. The optical detector 260 performs optical detection on the sample. The signal processing circuit 270 processes the signals output from the optical detector 60, and sends the processed signals to the controller 280. The controller 280 controls each part of the measuring unit 20, and communicates with the analyzing part 30. The controller 280 sends the information output from the detecting part 250 to the analyzing part 30. The controller 280 is configured by a microcomputer.

The analyzing part 30 analyzes the information of the components detected by the detecting part 250. The components in the urine sample analyzed by the analyzing part 30 are, for example, material components of urine. Material components of urine include, for example, red blood cells, white blood cells, epithelial cells, casts, bacteria, atypical cells, and white blood cell aggregate.

The analyzing part 30 is configured by a computer which has a CPU and memory. A computer program for analyzing the output of the detecting part 250 is installed in the analyzing part 30.

Figure 2:
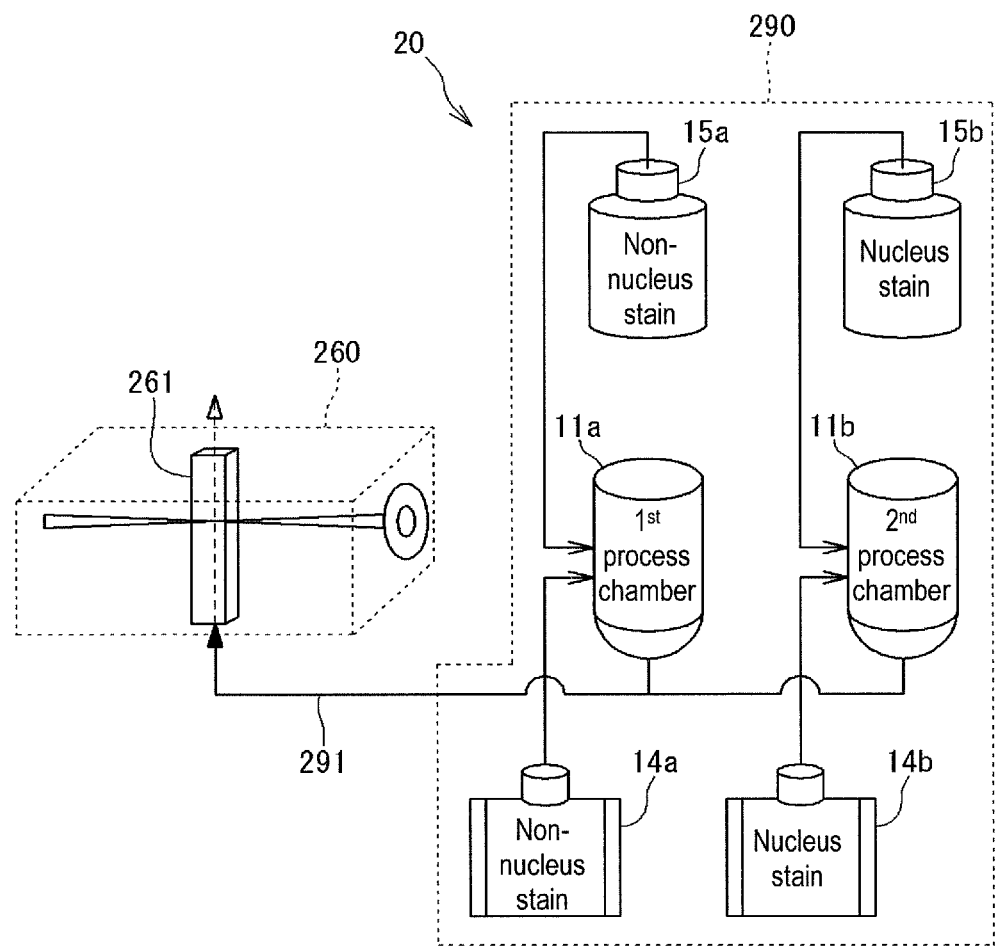
FIG. 2 is a structural view of the preparing part.

As shown in FIG. 2, the measuring unit 20 also has a preparing part 290 for preparing a measurement sample from a sample. The preparing part 290 respectively mixes the urine sample and reagent in a plurality of processing chambers 11*a* and 11*b* to which urine sample is dispensed. The plurality of processing chambers 11*a* and 11*b* include a first processing chamber 11*a* which performs processing to prepare a first measurement sample, and a second processing chamber 11*b* which performs processing to prepare a second measurement sample. The number of processing chambers also may be three or more.

The first measurement sample is obtained by mixing the urine sample and first reagents 15*a* and 14*a* in the first processing chamber 11*a*. The first reagents 15*a* and 14*a* are, for example, diluting liquid 15*a* and stain 14*a*. The stain 14*a* includes a fluorescent dye which stains material components that do not contain nucleic acid. In the first measurement sample, the material components in the urine sample are stained by the stain 14*a*. The first measurement sample is used to analyze particles that do not contain nucleic acid, such as red blood cells and casts in urine. The second measurement sample is obtained by mixing the urine sample and second reagents 15*b* and 14*b* in the second processing chamber 11*b*. The second reagents 15*b* and 14*b* are, for example, diluting liquid 15*b* and stain 14*b*. The stain 14*b* includes dye which stains nucleic acid. In the second measurement sample, the material components in the urine sample are stained by the stain 14*b*. The second measurement sample is used to analyze cells which contain nucleic acid, such as white blood cells, skin cells, fungi, bacteria, and atypical cells.

The first processing chamber 11*a* and second processing chamber 11*b* are connected by a sample delivery path to the flow cell 161 of the optical detector 260. The first measurement sample is supplied from the first processing chamber 11*a* to the flow cell 261 through the sample delivery path 291. The second measurement sample is supplied from the second processing chamber 11*b* to the flow cell 261 through the sample delivery path 291. The supplied measurement sample flows through the interior of the flow cell 261. The measurement samples are supplied to the flow cell 261 with the first measurement sample being first and the second measurement sample following the first measurement sample. The supplying of the measurement samples from the processing chambers 11*a* and 11*b* to the flow cell 261 is performed by the controller 280 controlling a pressure source and valves which are not shown in the drawing.

Figure 3:
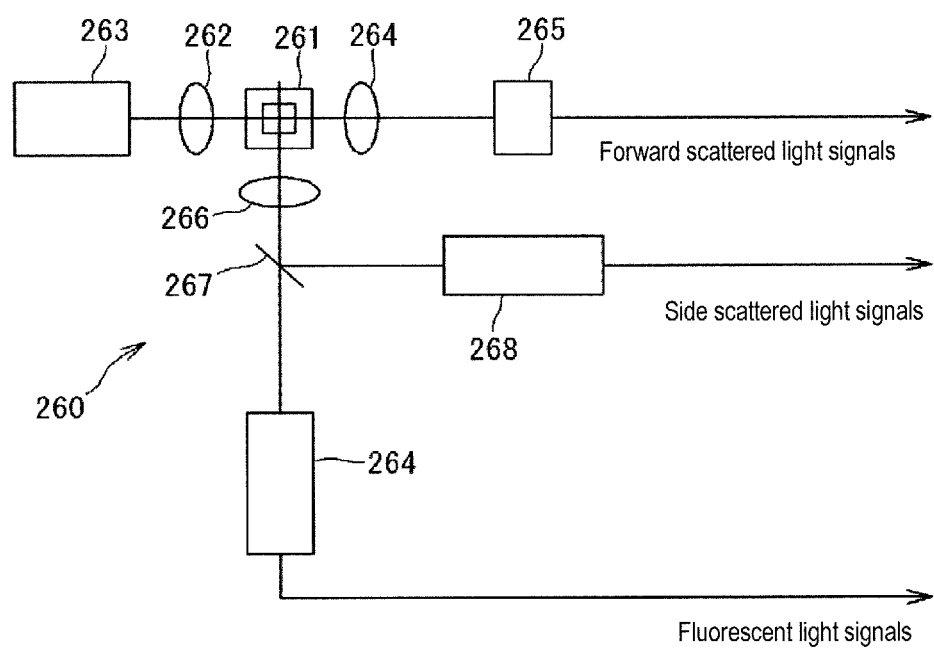
FIG. 3 is a structural view of the optical detecting part.

As shown in FIG. 3, the optical detector 260 is provided with a light irradiating part 263, and plurality of light receiving parts 265, 268, 269, in addition to the flow cell 161. The light irradiating part 263 is configured by, for example, a semiconductor laser light source. The light irradiating part 263 irradiates laser light on the measurement sample flowing through the flow cell 261. The plurality of light receiving parts 265, 268, 269 include a first scattered light receiving part 265, second scattered light receiving part 268, and fluorescent light receiving part 269. The light receiving parts 265, 268, 269 receive light given off from the components in the measurement sample which are irradiated by light.

The optical detector 260 is further provided with a condenser lens 262, collective lenses 264 and 266, and dichroic mirror 267. The condenser lens 262 collects the laser light emitted form the light irradiating part 263, and forms a beam spot on the measurement sample in the flow cell 261. The collective lens 264 collects the forward scattered light given off by the material components in the measurement sample into the first scattered light receiving part 265. The collective lens 266 collects the side scattered light and fluorescent light given off by the material components into the dichroic mirror 267. The dichroic mirror 267 reflects the side scattered light toward the second scattered light receiving part 268, and transmits the fluorescent light toward the fluorescent light receiving part 269.

The light receiving parts 265, 268, and 269 convert the received optical signal to electrical signals. The first scattered light receiving part 265 outputs forward scattered light signals, the second scattered light receiving part 268 outputs side scattered light signals, and the fluorescent light receiving part 269 outputs fluorescent light signals. Each signal represents temporal changes of the intensity of the light. Each signal is supplied to the signal processing circuit 270 shown in FIG. 1 through an amplifier and A/D converter (not shown in the drawing). The signal processing circuit 270 extracts characteristics parameters from each signal to be used in the analysis process performed by the analyzing part 30. The characteristics parameters include, for example, forward scattered light intensity, forward scattered light pulse width, side scattered light intensity, fluorescent light intensity, fluorescent light pulse width, and fluorescent light pulse area. The characteristics parameters are sent to the analyzing part 30 through the controller 280.

Returning to FIG. 1, the dispensing part 200 is provided with a first nozzle 111 which suctions and discharges urine sample, second nozzle 121 which suctions and discharges urine sample, and holding chamber 17 which temporarily holds the urine sample suctioned from the sample container 15 until the urine sample is dispensed to the processing chambers 11*a* and 11*b*.

The first nozzle 111 suctions the urine sample from the sample container 15, and discharges the suctioned urine sample to the holding chamber 17. The second nozzle 121 suctions the urine sample from the holding chamber 17, and discharges the sample to the plurality of processing chambers 11*a* and 11*b*, respectively. Measurement samples are prepared using the urine samples discharged from the second nozzle to the processing chambers 11*a* and 11*b*.

The dispensing part 200 further includes a sample suction circuit 150 for suctioning the sample through the first nozzle 111, and a dispensing circuit 180 for dispensing the sample to the processing chambers 11*a* and 11*b* through the second nozzle 121. The sample suctioning circuit 150 and dispensing circuit 180 are configured to have a fluid circuit. The fluid circuit of the embodiment is a pneumatic circuit. Note that the sample suctioning circuit 150 shown in FIG. 1 represents only the main structural elements. Detailed structure of the sample suctioning circuit 150 is shown in FIG. 4.

Figure 4:
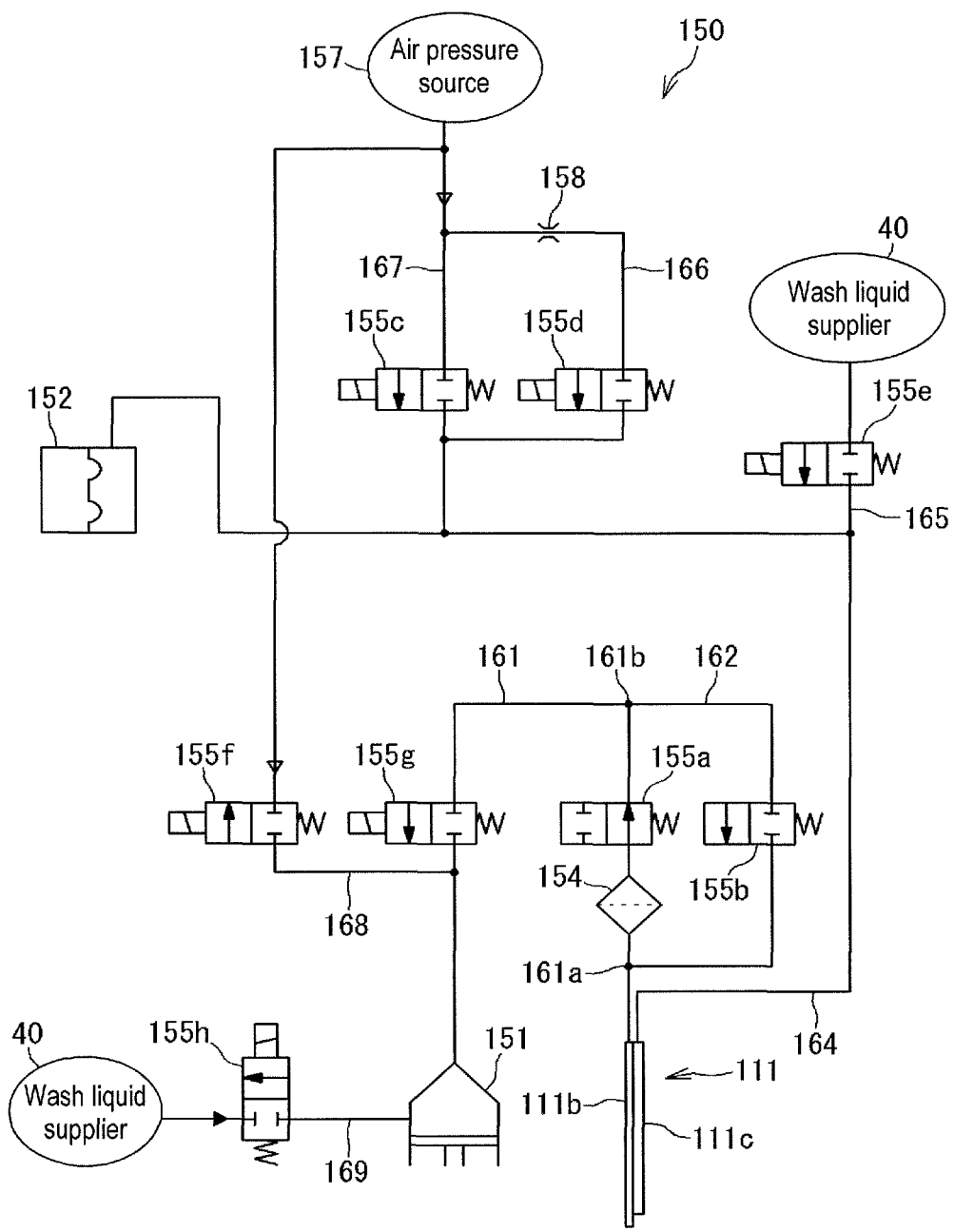
FIG. 4 is a circuit diagram of the sample suctioning circuit.

As shown in FIG. 1 and FIG. 4, the sample suctioning circuit 150 includes a first pressure source 151, a first flow path 161 from the first nozzle 111 to the first pressure source 151, and a second flow path 162 which branches off from the first flow path 161. The first pressure source 151 is, for example, a syringe pump. As shown in FIG. 1, the dispensing circuit 180 includes a pressure source 153, and a third flow path 163 from the second nozzle 121 to the pressure source 153. The pressure source 153 is, for example, a syringe pump.

The first nozzle 111 of the embodiment is configured to integratedly have a suctioning nozzle 111b and mixing nozzle 111c. The suctioning nozzle 111b and mixing nozzle 111c respectively have suction ports 111a and 111d at the lower end, and are respectively capable of suctioning and discharging sample from the suction ports 111a and 111d. The previously mentioned first flow path 161 is connected to the suctioning nozzle 111b. The sample suctioning circuit 150 is also provided with a second pressure source 152, and a fourth flow path 164 from the mixing nozzle 111c to the second pressure source 152. The second pressure source 152 is, for example, a diaphragm pump.

The second flow path 162 is a bypass path which branches from the first flow path 161 at a first position 161a of the first flow path 161, and conjoins the first flow path 161 at a second position 161b on the first pressure source 151 side from the first position 161a. A filter 154 for capturing foreign matter is provided between the first position 161a and 161b in the first flow path 161. Foreign matter in the urine sample suctioned from the suctioning nozzle 111b can be captured by the filter 154. Although the filter 154 prevents passage and captures the foreign matter in the urine sample, pores of sufficient diameter are provided to allow material components such as casts, epithelial cells and the like to pass through.

A first valve 155a is provided between the first position 161a and second position 161b of the first flow path 161. A second valve 155b is provided in the second flow path 162. The first valve 155a and the second valve 155b are, for example, solenoid valve. The first valve 155a and the second valve 155b switch the flow of urine sample being suctioned/discharged by the suctioning nozzle 111b. The operation of the first valve 155a, second valve 155b, other valves 155c, 155d, 155e, 155f, 155g, 155h shown in FIG. 7, and operation of pressure sources 151, 152, and 153 is controlled by the controller 280.

As shown in FIG. 1 and FIG. 4, the first valve 155a is in an open state when degaussed and in a closed state during excitation. The second valve 155b is in a closed state when degaussed and in an open state during excitation. Both valves 155a and 155b are degaussed when a urine sample is suctioned from a sample container 15. The urine sample is suctioned from the suctioning nozzle 111b by the suction pressure generated by the first pressure source 151. At this time, the suctioned urine sample is drawn through the first flow path 161 which has the open first valve 155a to the first pressure source 151 side and not the second flow path 162 which has the closed second valve 155b. The entirety of the suctioned urine sample moves past the second position 161b to the first pressure source 151 side. Since the suctioned urine sample passes through the filter 154 provided in the first flow path 161, foreign matter is captured by the filter 154.

Both valves 155a and 155b are excited when the suctioned urine sample is being discharged. The sample which has passed through the filter 154 and is between the second position 161b and the first position 161a is discharged from the suctioning nozzle 111b by the discharge pressure generated by the first pressure source 151. At this time, the sample bypasses the filter 154 by passing through the second flow path 162 which has the open second valve 155b and not the first flow path 161 which has the closed first valve 155a. During sample discharge foreign matter captured by the filter 154 is prevented from being discharged from the nozzle 111b with the urine sample by bypassing the filter 154.

The mixing nozzle 111c mixes the sample in the sample container 15 before the urine sample is suctioned from the sample container 15. The sample is allowed to flow from the mixing nozzle 111c to the fourth flow path 164 by the suction pressure generated by the second pressure source 152, then the sample in the fourth flow path 164 is again returned from the mixing nozzle 111c to the sample container 15 by the discharge pressure generated by the second pressure source 152. The sample is thoroughly mixed by the repeated suction and discharge by the mixing nozzle 111c. The fourth flow path 164 is a formed as a wider flow path than the first flow path 161 and second flow path 162. Thus, the suction and discharge for mixing is performed efficiently. Note that air supplied from the air pressure source 157 also can be used to mix the sample.

Although a syringe pump suited to provide a precise amount of sample is used as the first pressure source 151, a diaphragm pump is used as the second pressure source 152 in the embodiment. The diaphragm pump 152 can perform the mixing in a short time since its suction and discharge speeds are faster and several suctions and discharges can be performed quickly.

The dispensing circuit 180 shown in FIG. 1 suctions the sample in the holding chamber 17 through the second nozzle 121, and dispenses the suctioned sample to the processing chambers 11a and 11b. The sample in the holding chamber 17 is allowed to flow from the second nozzle 121 top the third flow path 163 by the suction pressure generated by the pressure source 153. Thereafter, the sample in the third flow path 163 is discharged to the plurality of processing chambers 11a and 11b by the discharge pressure generated by the pressure source 153. The dispensing circuit 180 does not require a filter 154 to capture foreign matter since the sample is suctioned after the foreign matter has been removed. That is, the third flow path 163 is a filterless flow path.

The second nozzle 121 is configured to have an internal diameter that is smaller than the flow path diameter within the suctioning nozzle 111a of the first nozzle 111. Sample possibly containing foreign matter can be efficiently suctioned by enlarging the suctioning nozzle 111a. However, a precise amount of sample can be obtained by narrowing the second nozzle 121. The second nozzle 121 has a low possibility of becoming clogged by foreign matter even if narrowed because foreign matter has been removed from the sample to be suctioned and discharged.

The sample suctioning circuit 150 shown in FIG. 4 is provided with many valves 155c, 155d, 155e, 155f, 155g, and 155h in addition to the first valve 155a and second valve 155b in order to wash the first nozzle 111 and flow paths 161, 162, 164 in addition to suctioning, discharging, and mixing sample. The operation of the sample suctioning circuit 150 is described below according to FIGS. 5 through 18. The operations described below are performed by controls performed by the controller 280.

2. Operation of Sample Suctioning Circuit 2.1 Standby

Figure 5:
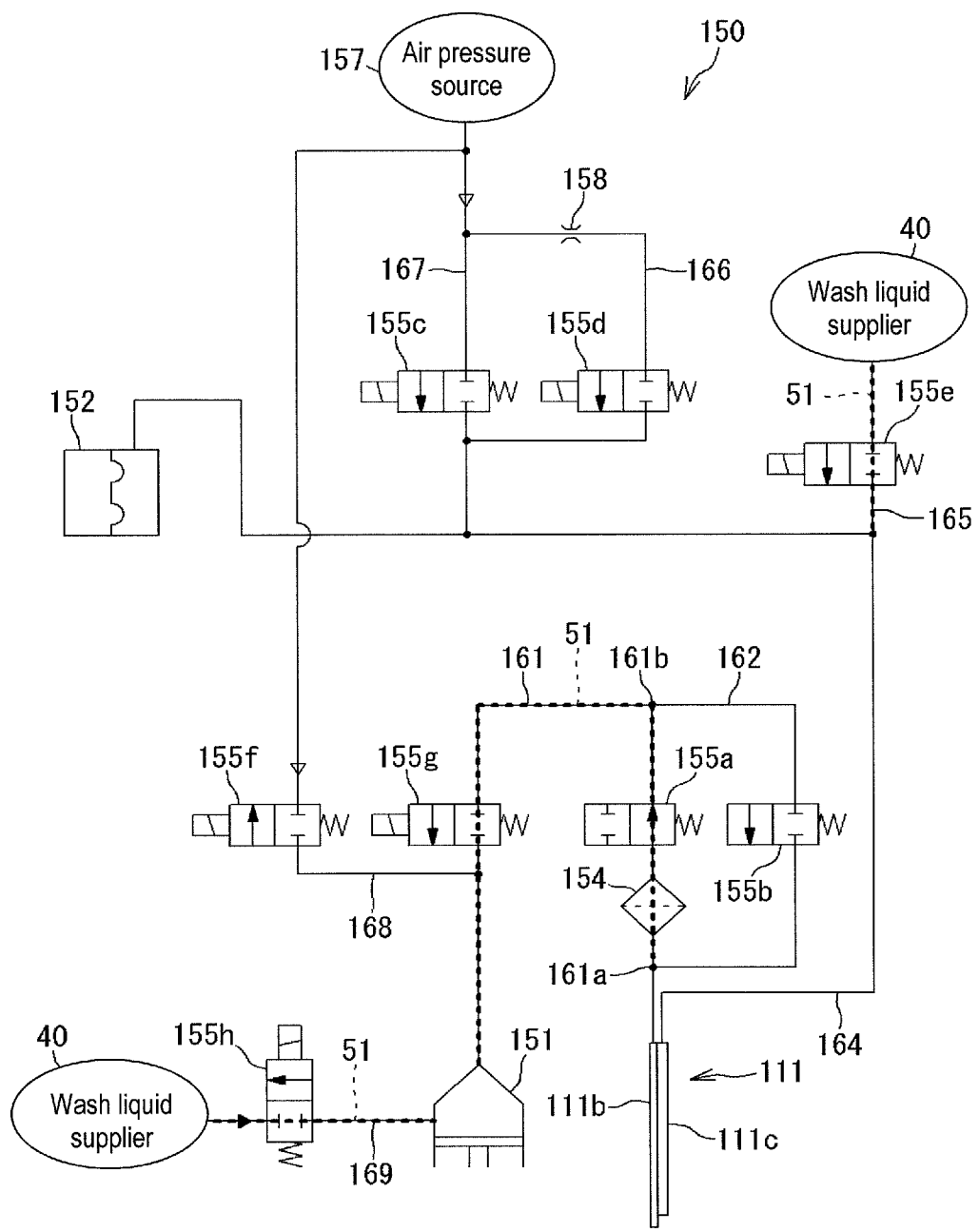
FIG. 5 illustrates the sample suctioning circuit in the standby state.

As shown in FIG. 5, washing solution 51 consisting of diluting liquid fills the majority of the first flow path 161 from the suctioning nozzle 111b of the first nozzle 111 to the first air pressure source 151 in the sample suctioning circuit 150 in the standby state before the sample is suctioned. Accordingly, between the first position 161a and the second position 161b in the first flow path 161 is filled with liquid. In the first flow path 161, air fills from the near the first position 161a to the suctioning nozzle 111b side. Note that washing liquid fills from the wash liquid supplier 40 to the flow path 165 which conjoins the fourth flow path 164 and from the wash liquid supplier 40 to the flow path 169 to the first pressure source 151. In FIG. 5 the part which is not filled with washing liquid is filled with air. For example, the second flow path 162 is filled with air.

2.2 Mixing

The first nozzle 111 is actuated by a nozzle drive part not shown in the drawing to penetrate into the sample container 15. Sample mixing is performed by the mixing nozzle 111c before the sample is suctioned by the suctioning nozzle 111b of the first nozzle 111. Mixing is accomplished by performing suction/discharge mixing to mix the sample and bubble mixing by blowing air into the sample in the sample container 15 by suctioning and discharging the sample from the mixing nozzle 111c.

Figure 6:
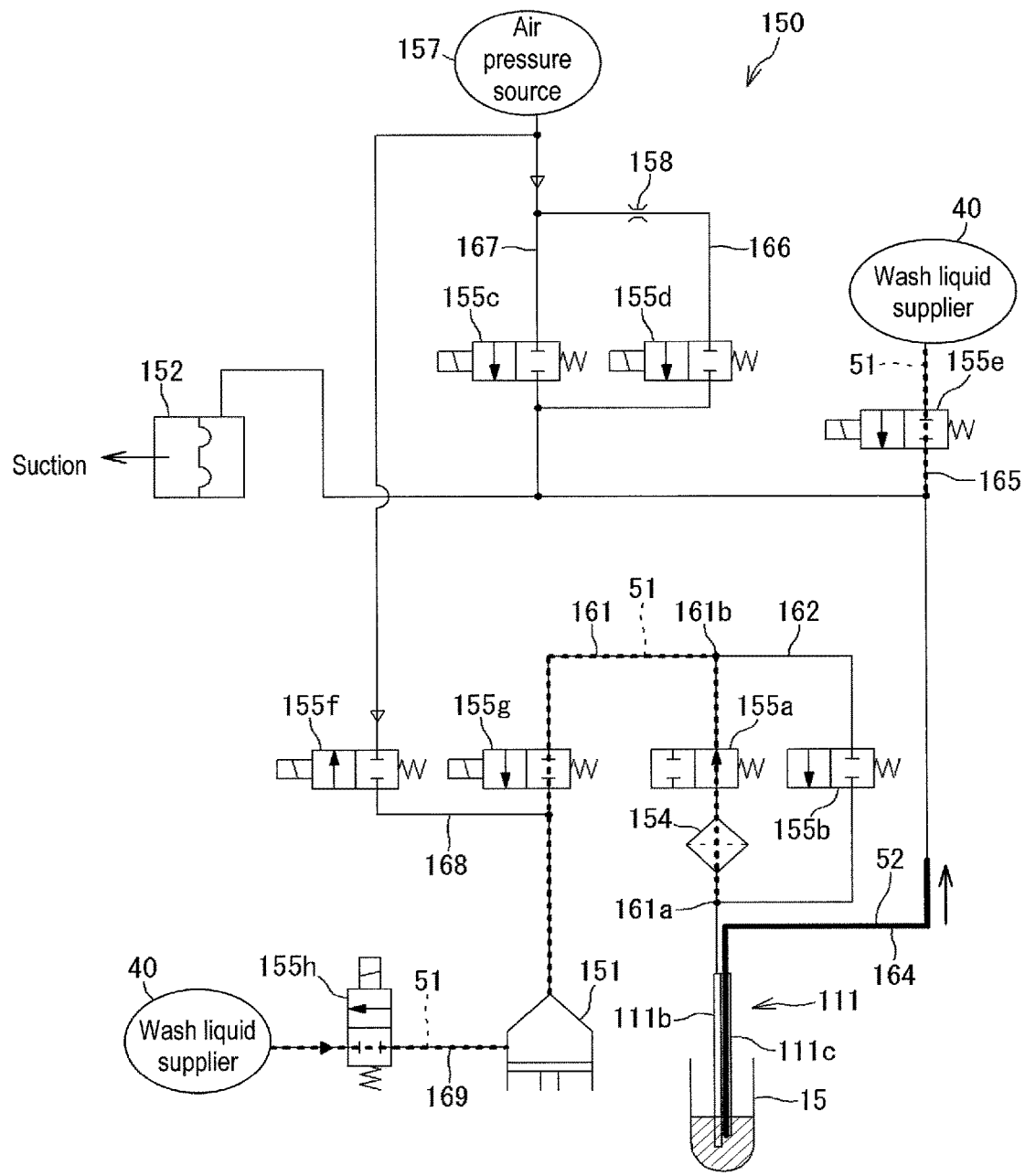
FIG. 6 illustrates the sample suctioning circuit during sample mixing.
Figure 7:
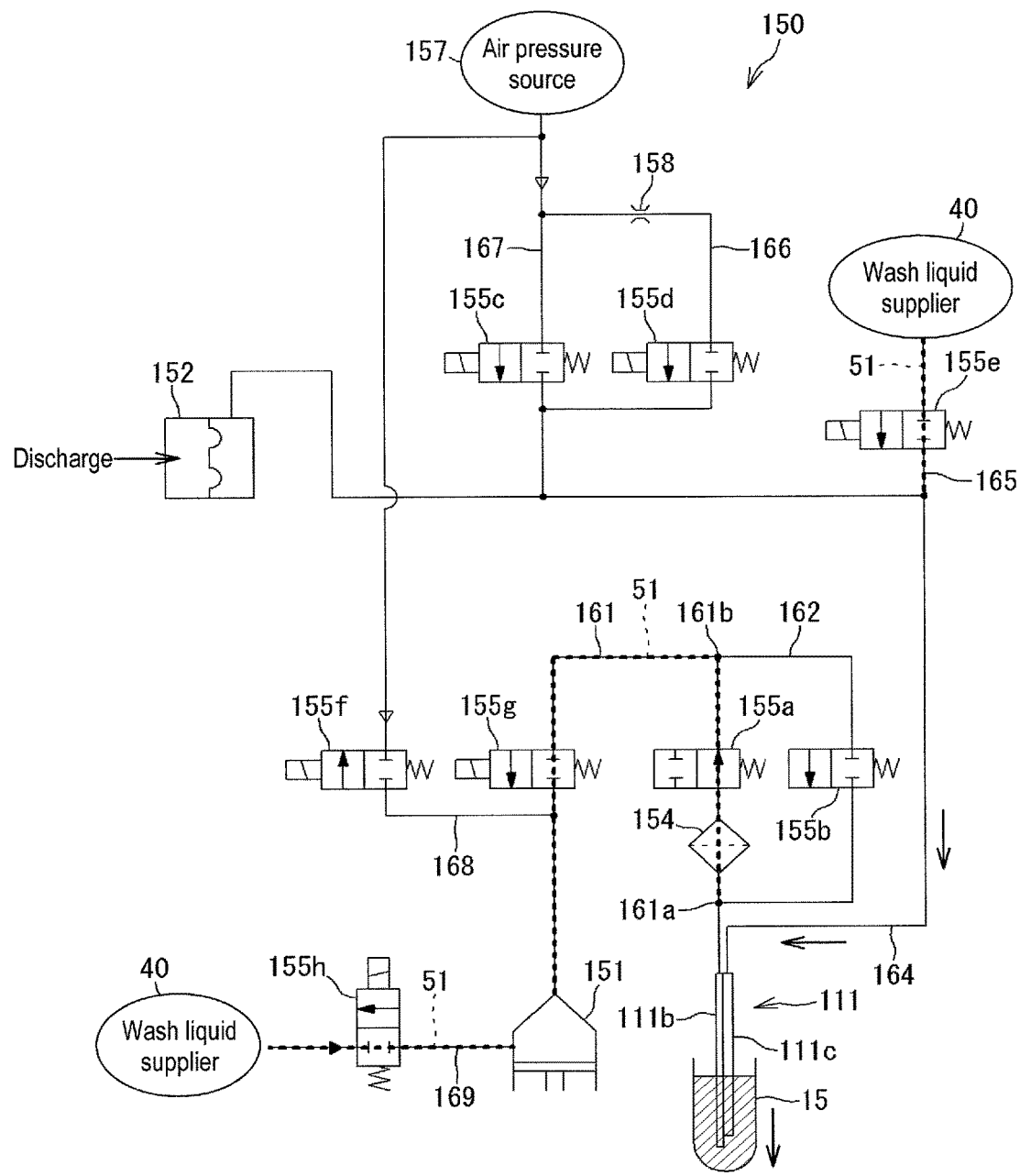
FIG. 7 illustrates the sample suctioning circuit during sample mixing.

The urine sample in the sample container 15 is suctioned from the mixing nozzle 111c by suction pressure generated by the second pressure source 152 to perform suction/discharge mixing. As shown in FIG. 6, the urine sample 52 suctioned form the mixing nozzle 111c flows into the fourth flow path 164. As shown in FIG. 7, the urine sample 52 in the fourth flow path 164 is thereafter returned again from the mixing nozzle 111c to the sample container 15 by the discharge pressure generated by the second pressure source 152. Suction/discharge mixing is accomplished by suctioning and discharging by the mixing nozzle 111c.

Figure 8:
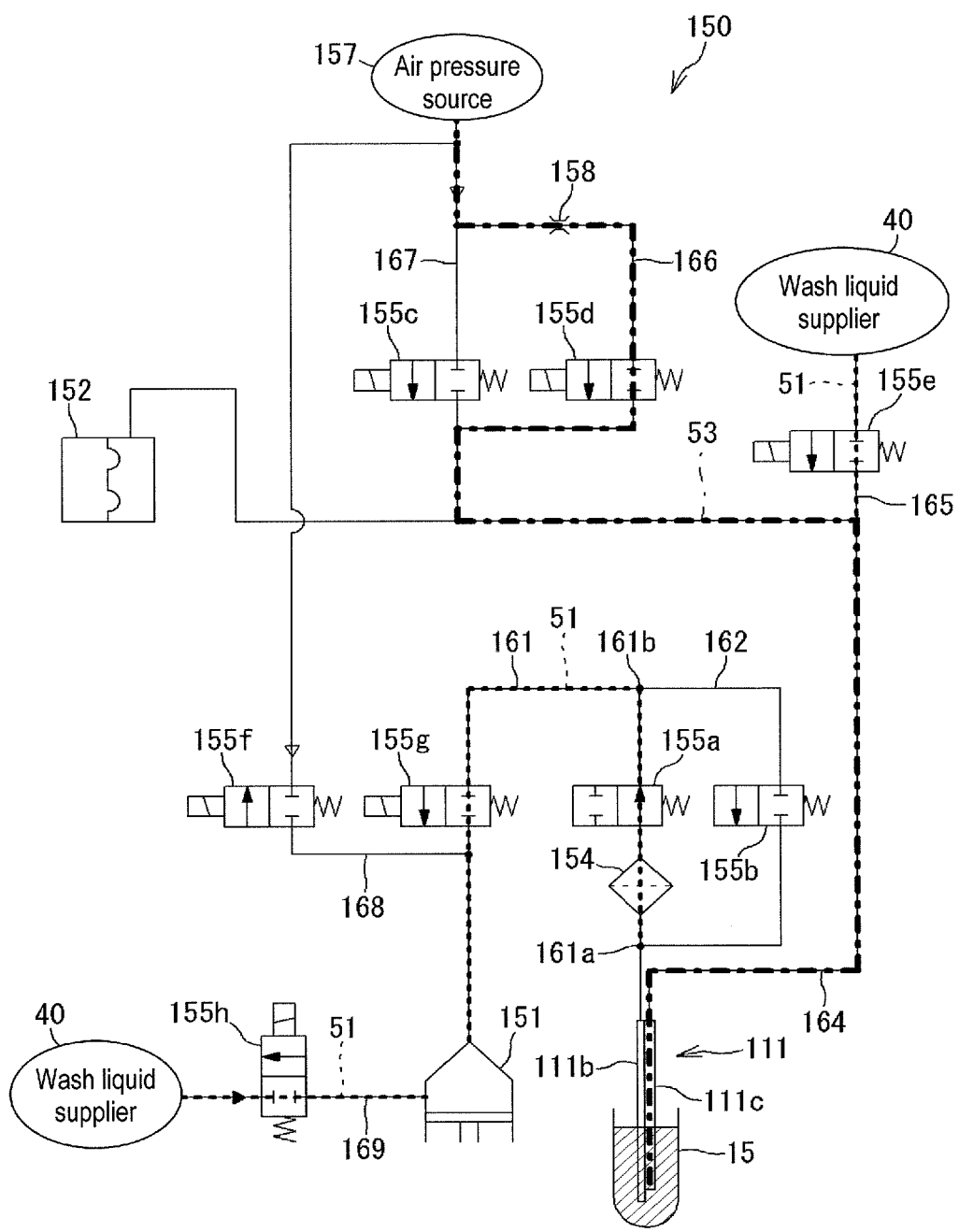
FIG. 8 illustrates the sample suctioning circuit during sample mixing.

As shown in FIG. 8, the air 53 supplied from the air pressure source 157 is discharged through the flow path 116 and fourth flow path 164 and from the mixing nozzle 111c to accomplish bubble mixing. The urine sample is mixed by the bubbles formed in the urine sample by the air discharged from the mixing nozzle 111c. When performing bubble mixing, the valve 155d is opened in the flow path 166 which is one flow path to the air pressure source 157, and the air supplied from the air pressure source 157 passes through the flow path 166 to the fourth flow path 164. An orifice 158 for constricting the airflow is provided in the flow path 166. The bubbles can be made smaller by constricting the airflow via the orifice 158. Mixing is more reliably performed by repeating several sets of suction/discharge mixing and bubble mixing.

2.3 Suction

Figure 9:
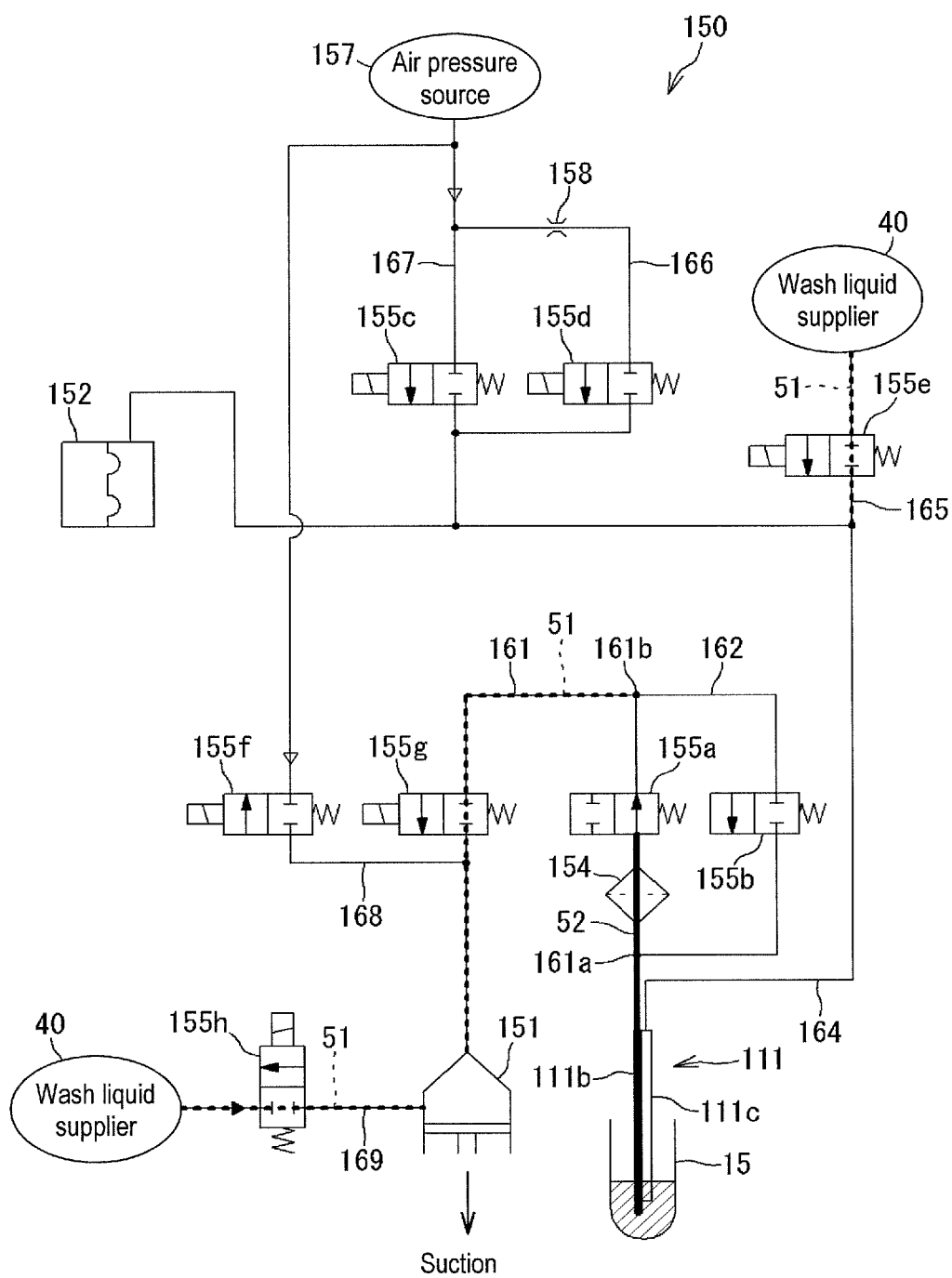
FIG. 9 illustrates the sample suctioning circuit during sample suctioning.

After mixing, the sample is suctioned from the sample container 15 by the suctioning nozzle 111b. During suctioning, the valve 155g provided in the first flow path 161 to the first pressure source 151 is actuated to the open state. The urine sample within the sample container 15 is suctioned from the suctioning nozzle 111b by the suction pressure generated by the first pressure source 151. As shown in FIG. 9, the suctioned urine sample 52 is drawn through the first flow path 161, in which the first valve 155a is in the open state, to the first pressure source 151 side. The amount suctioned by the first pressure source 151 is, for example, 450 µL. Since the suctioned urine sample 52 passes through the filter 154 provided in the first flow path 161, foreign matter in the urine sample 52 is captured by the filter 154. When the required amount has been suctioned, the valve 155g is closed and the suctioning is temporarily stopped.

Figure 10:
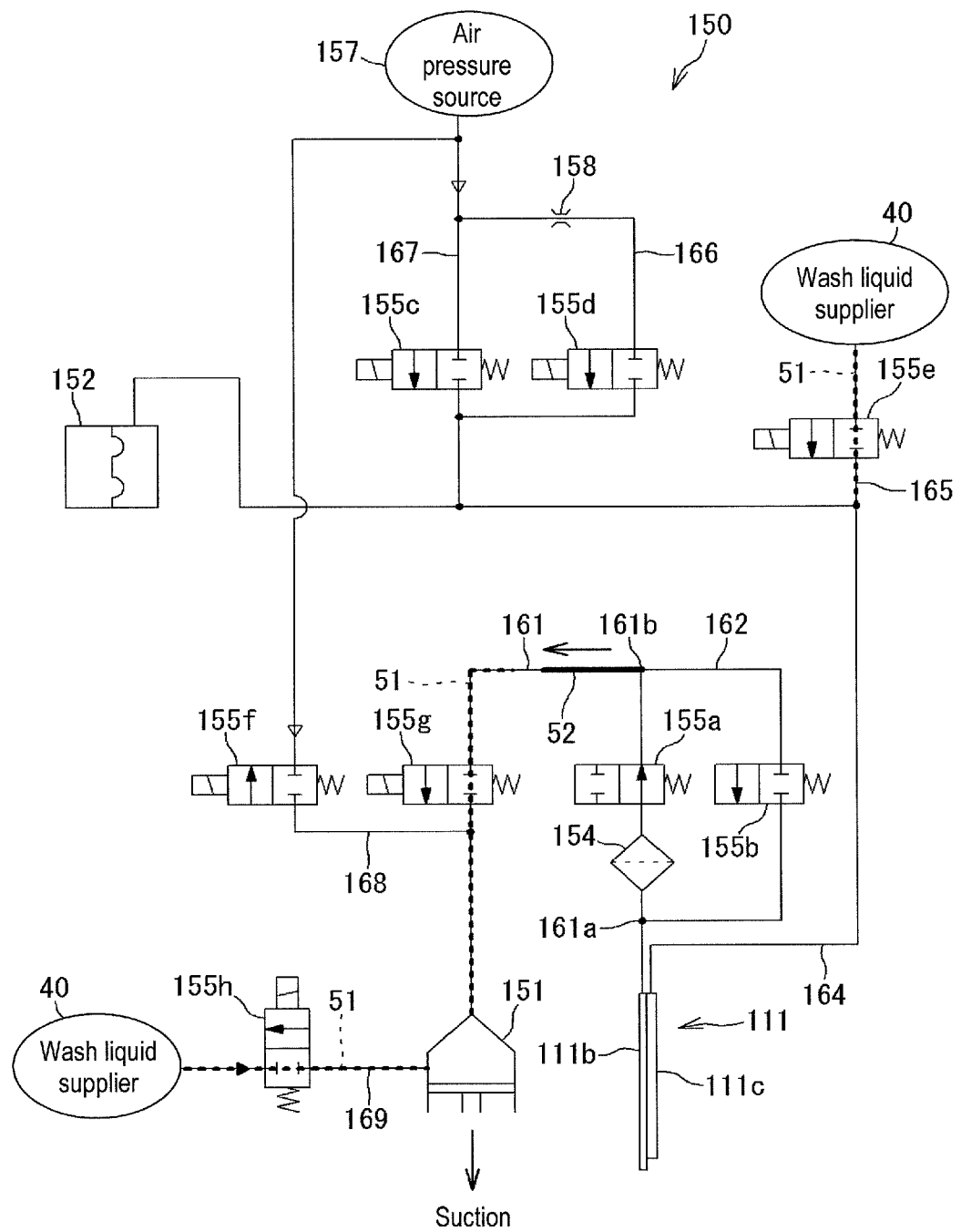
FIG. 10 illustrates the sample suctioning circuit during sample suctioning.

Thereafter, the first nozzle 111 is retracted from the sample container 15 by a nozzle drive part which is not shown in the drawing. With the first nozzle 111 retracted from the sample container 15, the valve 155g is opened, and further suctioning is performed by the suction pressure generated by the first pressure source 151. In this further suctioning, the suctioning nozzle 111b of the first nozzle 111 suctions air. This air suctioning is atmospheric air suctioning. As shown in FIG. 10, the previously suctioned urine sample 52 is moved further to the first pressure source 151 side by the air suctioning. Air suctioning is performed until all of the suctioned urine sample 51 is moved to the first pressure source 151 side from the second position 161b of the flow path 161. The entirety of the suctioned urine sample 51 can be discharged from the second flow path 162 by continuing the suction operation by the suctioning nozzle 111 until all the urine sample 51 is moved to the first pressure source 151 side from the first position 161b.

2.4 Discharge

Figure 11:
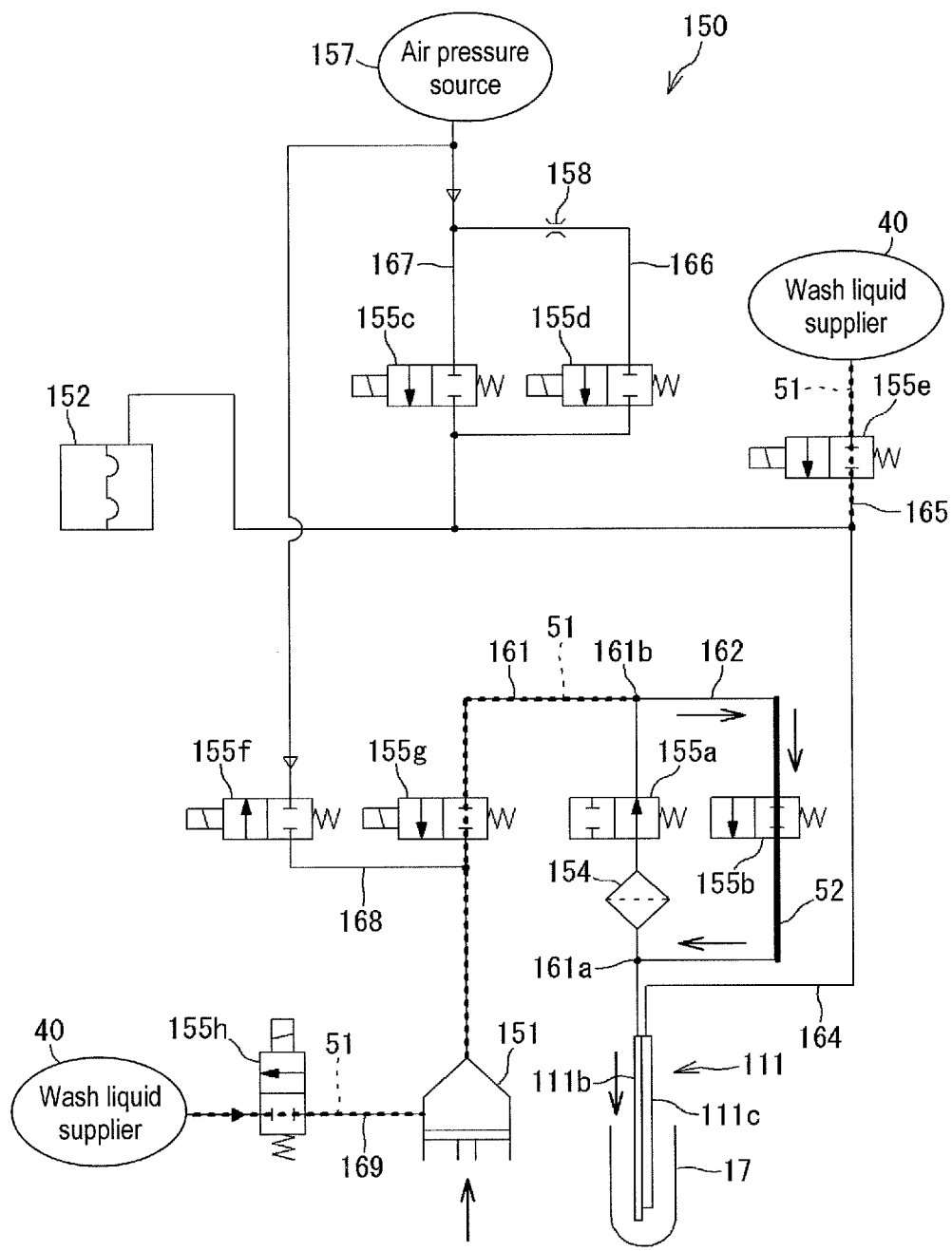
FIG. 11 illustrates the sample suctioning circuit during sample discharging.
Figure 12:
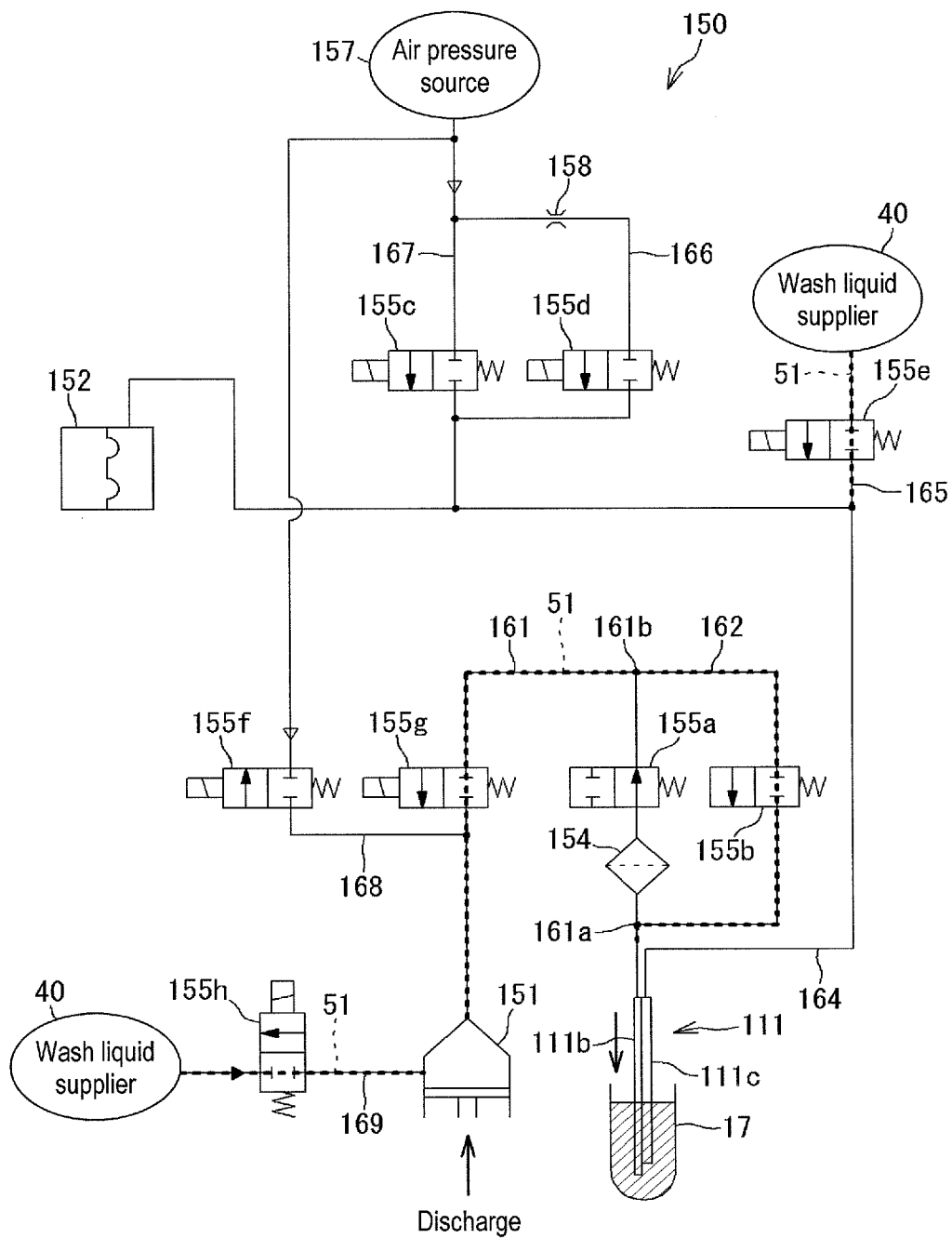
FIG. 12 illustrates the sample suctioning circuit during sample discharging.

Thereafter, the first nozzle 111 enters the holding chamber 17 by a nozzle drive part which is not shown in the drawing. During discharging, the valve 155g provided in the first flow path 161 to the first pressure source 151 is actuated to the closed state. The first valve 155a is actuated and closed, and the second valve 155b is actuated and opened. Thus, the sample travel path between the first position 161a and second position 161b is changed from the first flow path 161 to the second flow path 162. The urine sample 52 is discharged from the suctioning nozzle 111b to the holding chamber 17 by the discharge pressure generated by the first pressure source 151. As shown in FIG. 11, during discharge the urine sample 52 passes through the second flow path 162 via the open second valve 155b and flows to the suctioning nozzle 111b side. As shown in FIG. 12, discharge ends when all the suctioned urine sample 52 is moved to the holding chamber 17.

2.5 Washing

The first nozzle 111 which has finished sample discharging enters the wash tank 18 by a nozzle drive part which is not shown in the drawing. The washing process includes washing of the first nozzle 111, washing of the flow paths 161 and 162 used for sample discharge, washing of the fourth flow path 164 used for mixing, blowing air to the fourth flow path 164 used for mixing and flow paths 161 and 162 used for sample discharge, and washing of the flow path 161 used for sample suctioning.

Figure 13:
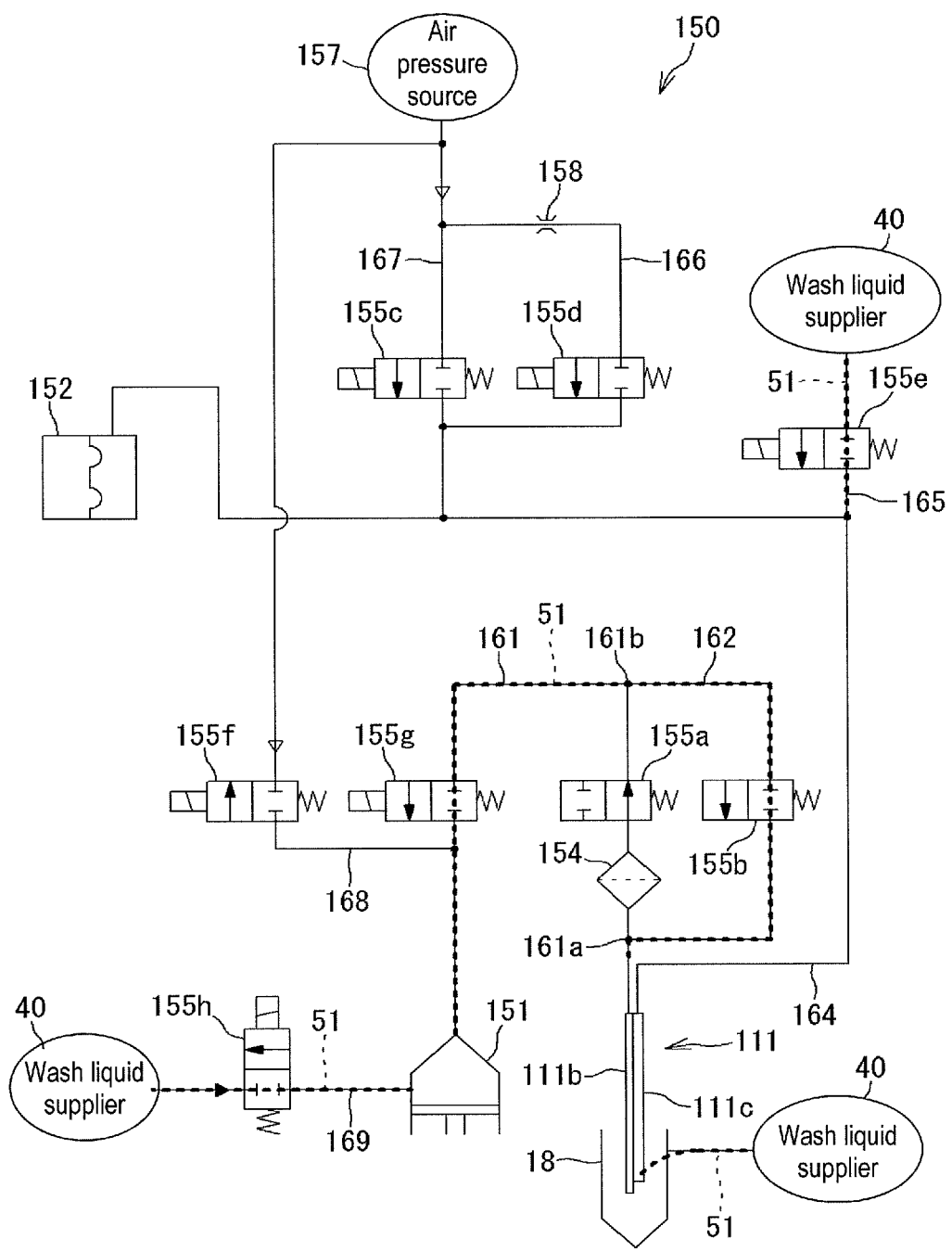
FIG. 13 illustrates the sample suctioning circuit during washing.

As shown in FIG. 13, washing liquid, which is solution used for washing, is supplied from the wash liquid supplier 40 to the wash tank 18 to wash the first nozzle 111. The exterior of the first nozzle 111 is washed in this way. Note that the washing liquid supplied to the wash tank 18 is discharged from a drain which is not shown in the drawing.

Figure 14:
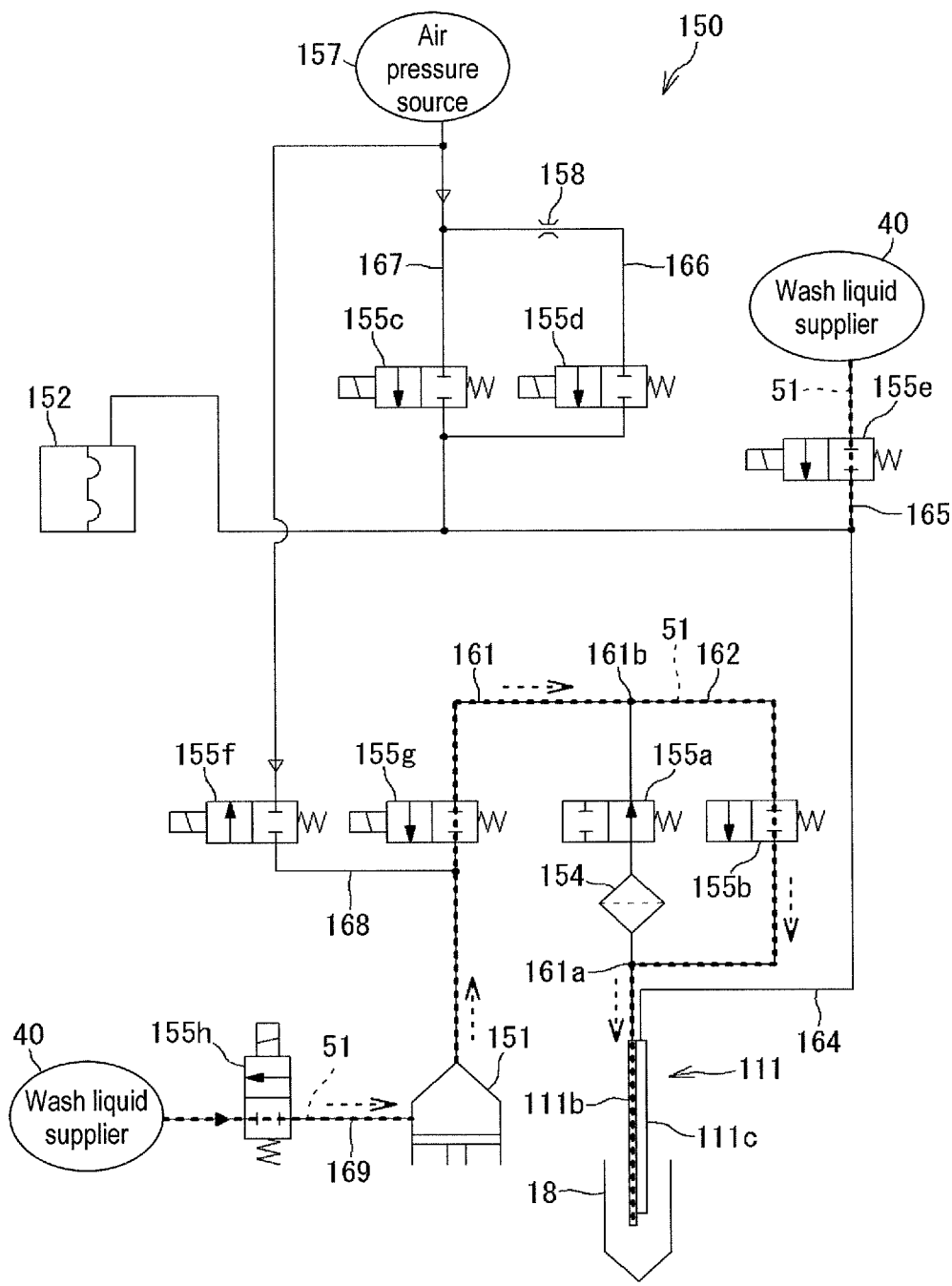
FIG. 14 illustrates the sample suctioning circuit during washing.

Next, the flow paths 161 and 162 used for sample discharge are washed. The flow path used for sample discharge is mainly the second flow path 162, and the part other than from the first position 161a to the second position 161b of the first flow path is also washed in conjunction with washing the second flow path 162. The interior surface of the suctioning nozzle 111b of the first nozzle 111 is also washed. When washing the flow paths 161 and 162 used for sample discharge, the first valve 155a is actuated to close, and the second valve 155b is actuated to open. The valve 155g provided in the flow path 169 between the first pressure source 151 and the wash liquid supplier 40, and the valve 155h provided in the first flow path 161 are actuated to the open state. As shown in FIG. 14, the washing liquid 51 which is supplied from the wash liquid supplier 40 passes through the second flow path 162, reaches the suctioning nozzle 111b of the first nozzle 111, and is discharged to the wash tank 18 by the discharge pressure generated by the first pressure source 151. The flow paths 161 and 162 used for sample discharge are washed by flowing the washing liquid 51 in this way.

Figure 15:
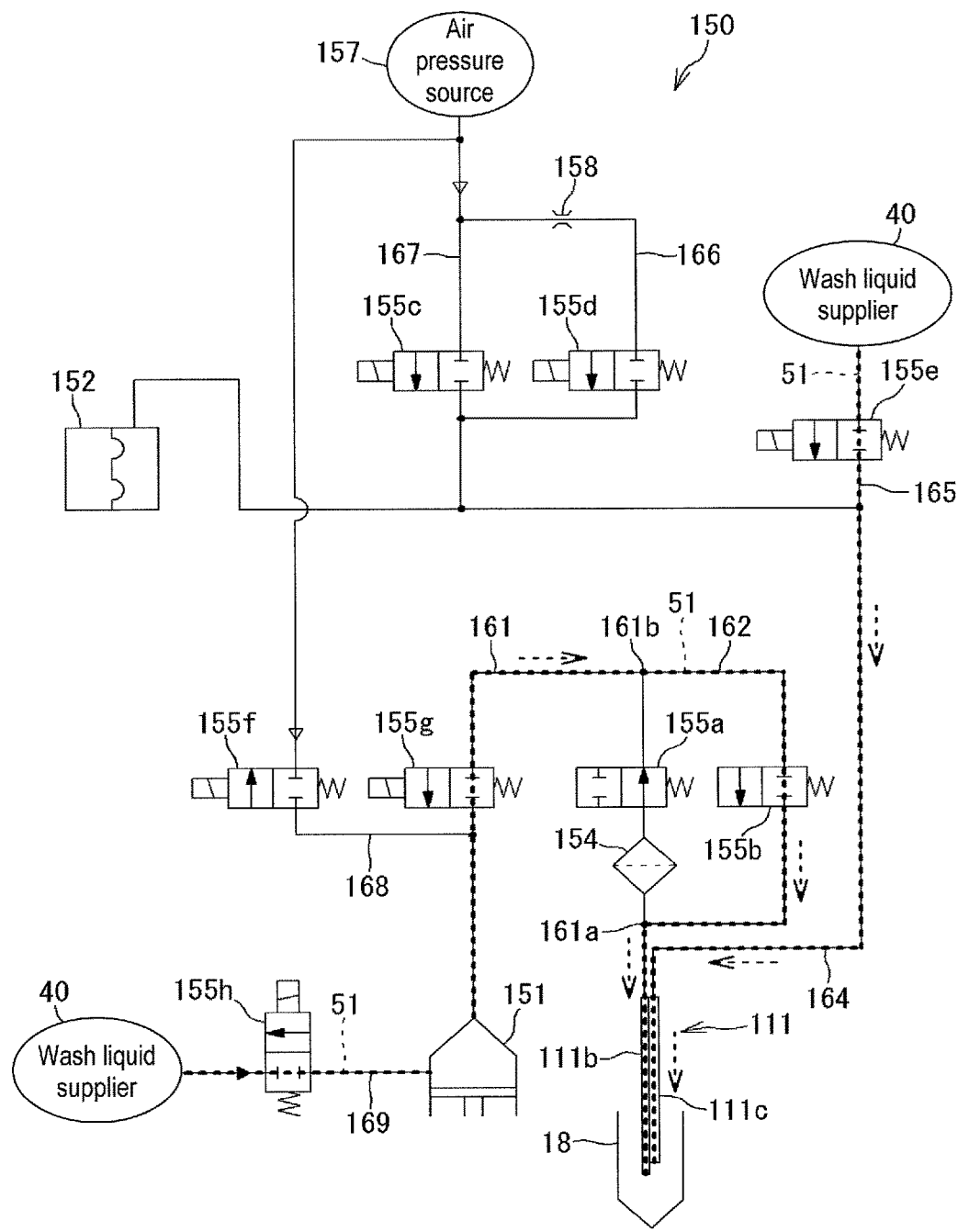
FIG. 15 illustrates the sample suctioning circuit during washing.
Figure 16:
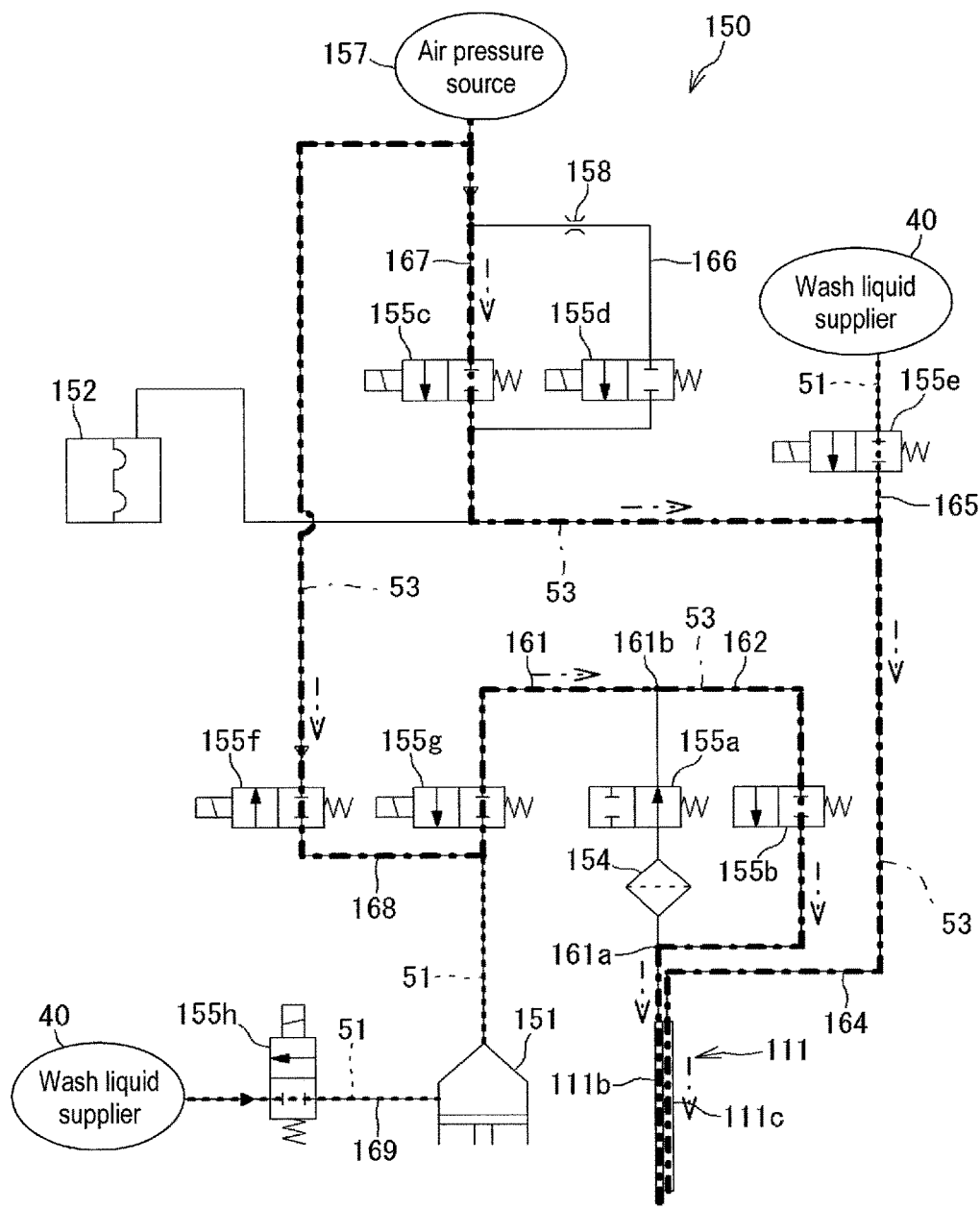
FIG. 16 illustrates the sample suctioning circuit during washing.

As shown in FIG. 15, the valve 155e which is provided in the flow path 165 from the wash liquid supplier 40 to the fourth flow path 164 also is actuated to the open state. As a result, the washing liquid 51 flows from the wash liquid supplier 40 through the flow path 165 to the fourth flow path 164. The washing liquid which reaches the fourth flow path 164 is discharged from the mixing nozzle 111c to the wash tank 18. The interior surface of the mixing nozzle 111c and the fourth flow path 164 which is the flow path used for mixing are washed in this way.

Next, air is blown to the fourth flow path 164 used for mixing and the flow paths 161 and 162 used to discharge sample, as shown in FIG. 6. The blown air removes the washing liquid from the flow paths 161 and 162 for which washing is completed. The first valve 155a is actuated and closed, and the second valve 155b is actuated and opened when air is blown. The valve 155c provided in the flow path 167 connected to the air pressure source 157 is actuated to the open state, and the valve 155f provided in the flow path 168 connected to the air pressure source 157 also is actuated to the open state. The valve 155g provided in the first flow path 161 also is actuated to the open state. The air supplied from the air source 157 passes through the flow path 168, flows into the first flow path 161, passes through the second flow path 162 and is discharged from the suctioning nozzle 111b. The air supplied from the air source 157 also passes through the flow path 167, flows into the fourth flow path 164 and is expelled from the mixing nozzle 111c.

Figure 17:
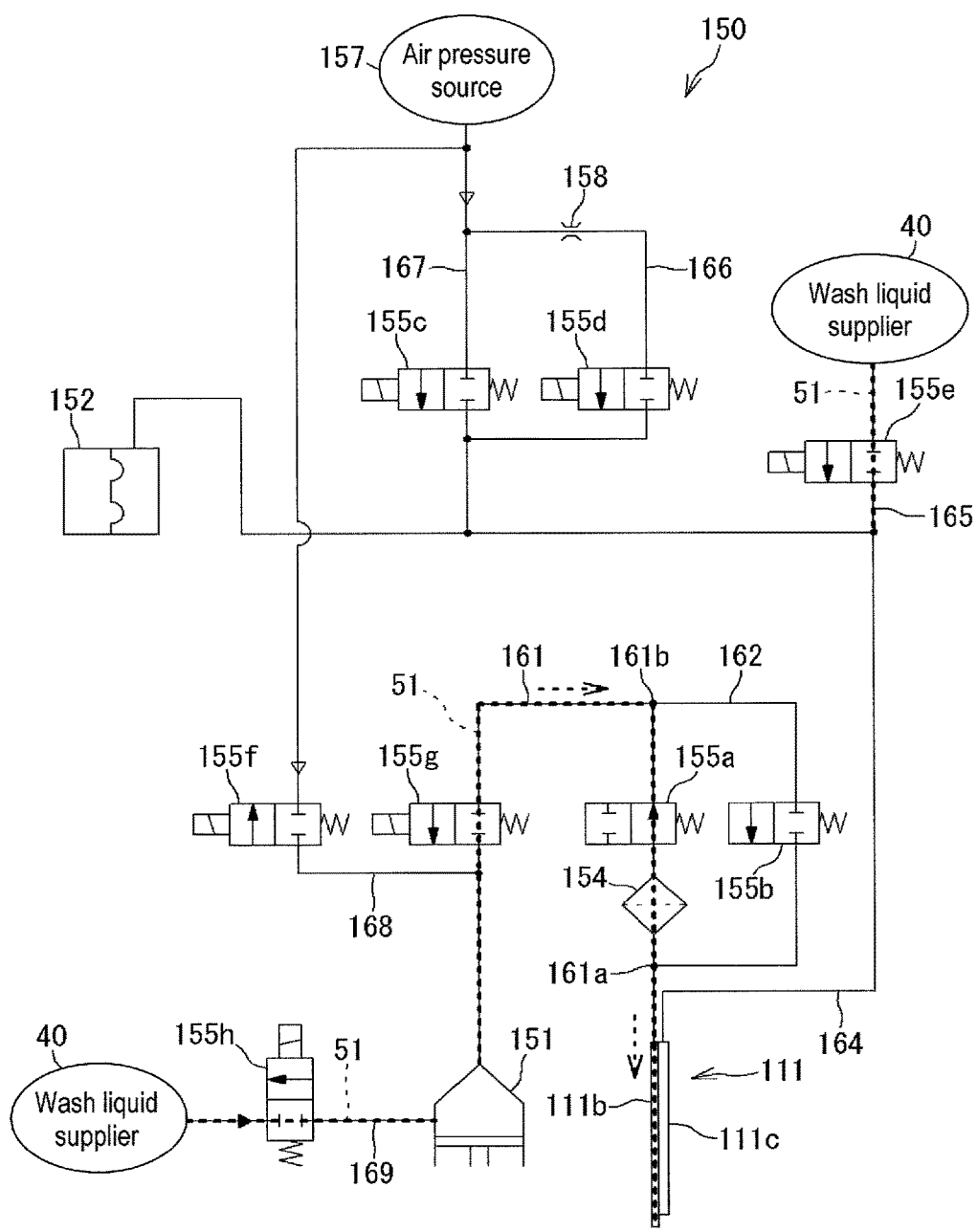
FIG. 17 illustrates the sample suctioning circuit during washing.

Thereafter, the first flow path 161 used for sample suction is washed. Although the primary purpose of washing in this case is washing between the first position 161a and second position 161b which has not yet been washed in the first flow path 161, the entire first flow path 161 is actually washed. The first valve 155a is opened and the second valve 155b is closed when washing the first flow path 161. The valve 155g is also open. As shown in FIG. 17, the washing liquid 51 which is supplied from the wash liquid supplier 40 passes through the first flow path 161, reaches the suctioning nozzle 111b of the first nozzle 111, and is discharged to the wash tank 18 by the discharge pressure generated by the first pressure source 151. The flow path 161 is washed by flowing the washing liquid 51 in this way. Foreign matter captured by the filter 154 also is discharged to the wash tank 18 by the washing liquid.

2.6 Air Gap Production

Figure 18:
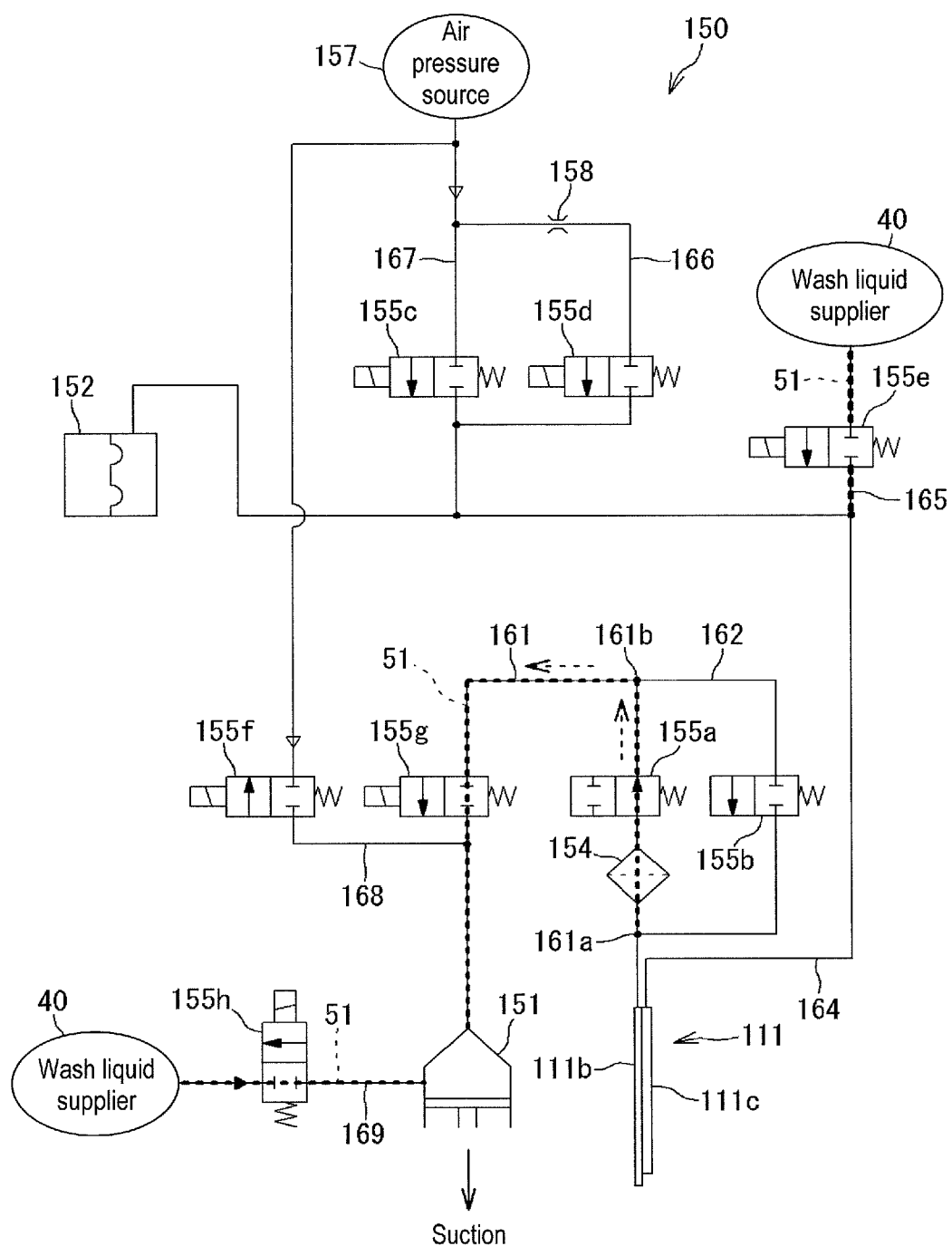
FIG. 18 illustrates the sample suctioning circuit during air gap production.

When washing of the first flow path 161 is completed, washing liquid fills the suctioning nozzle 111b to the tip. When the next sample is suctioned in this state, there is concern that the sample may come into contact with the residual washing liquid 51 in the suctioning nozzle 111b. Therefore, air is suctioned from the suctioning nozzle 111b to ensure there is an air gap between the washing liquid 51 and the next suctioned sample. While suctioning air the first valve 155a is open and the second valve 155b is closed. The valve 155g is also open. As shown in FIG. 18, suctioning air is the suctioning of air by the suctioning nozzle 111b in which the washing liquid 51 within the first flow path 161 is drawn to the first pressure source 151 side by the suctioning pressure generated by the first pressure source 151. The sample suctioning circuit 150 is returned to the standby state shown in FIG. 5 by the suctioning of air, and the next sample can be suctioned and the like. As previously described, between the first position 161a and second position 161b of the first flow path 161 is filled with washing liquid, and the second flow path 162 is filled with air in the standby state, and this is a state suited for the suctioning and discharging of the next sample.

The controller 280 can perform suctioning and discharging of a plurality of samples by the first nozzle 111 by repeating the series of operations shown in FIGS. 5 through 18.

Note that the structure is not limited to discharging the urine sample using the bypass second flow path 162 in order to prevent the foreign matter captured by the filter 154 from being discharged from the suctioning nozzle 111b with the urine sample. The filter 154 does not need to be positioned on the path of travel of the urine sample, inasmuch as, for example, the filter 154 also may be configured to retract from the first flow path 161 when the urine sample is discharged from the first flow path 161.

What is claimed is:

1. A urine sample analyzer comprising:
   a nozzle which suctions and discharges a urine sample;
   a pressure source which generates pressures to suction and discharge the urine sample;
   a first flow path from the nozzle to the pressure source;
   a second flow path which branches from the first flow path at a first position of the first flow path, and which conjoins with the first flow path at a second position on the pressure source side of the first position;
   a filter for capturing foreign matter, which is placed in the first flow path between the first position and the second position;
   valves which control a flow of fluid in a flow path circuit that includes the first flow path and the second flow path;
   a controller which controls the valves so that the urine sample suctioned by the nozzle passes through the filter, and the urine sample that has passed through the filter bypasses the filter by passing through the second flow path and is discharged from the nozzle;
   a detector which detects information of material components in the urine sample discharged by the nozzle; and
   an analyzing part which analyzes the information of the material components detected by the detector.

2. The urine sample analyzer of claim 1, wherein the controller controls the valves to move all the suctioned urine sample from the second position to the pressure source side.

3. The urine sample analyzer of claim 2, wherein the controller controls the valves to continue a suction operation by the nozzle until all the urine sample is moved from the second position to the pressure source side.

4. The urine sample analyzer of claim 1, wherein the first flow path is filled with liquid at least between the first position and the second position, and the second flow path is filled with air, prior to suctioning the urine sample.

5. The urine sample analyzer of claim 1, wherein the controller controls the valves to flow liquid in a course through the second flow path to the nozzle to wash the second flow path after the urine sample has been discharged from the nozzle, and thereafter flows liquid in a course through the first position and the second position in the first flow path to the nozzle to wash between the first position and the second position of the first flow path.

6. The urine sample analyzer of claim 5, wherein the controller controls the valves to fill liquid between the first position and the second position in the first flow path and fill air in the second flow path after washing between the first position and the second position in the first flow path, and thereafter controls the valves to suction a next urine sample.

7. The urine sample analyzer of claim 1 further comprising:
a holding chamber for holding the urine sample that has been discharged from the nozzle;
a second nozzle for suctioning the urine sample from the holding chamber;
wherein the second nozzle has a smaller flow path diameter than the nozzle.

8. The urine sample analyzer of claim 7 further comprising:
a third flow path connected to the second nozzle;
wherein the third flow path is a filterless flow path which is not provided with a filter to capture foreign matter.

9. The urine sample analyzer of claim 1, wherein the pressure source is a syringe pump.

10. The urine sample analyzer of claim 1, wherein the nozzle is configured to suction the urine sample from a sample container;
the controller controls a discharge of the urine sample which has been suctioned from the sample container by the nozzle back to the sample container in order to mix the urine sample in the sample container.

11. The urine sample analyzer of claim 10, wherein the nozzle comprises a mixing nozzle which mixes the urine sample in the sample container, and a suction nozzle which suctions the urine sample from the sample container after the urine sample is mixed.

12. The urine sample analyzer of claim 11 further comprising:
a diaphragm pump for generating a pressure for mixing the urine sample in the sample container.

13. The urine sample analyzer of claim 1, wherein the detector comprises:
a flow cell through which flows a measurement sample prepared from reagent and the urine sample suctioned by the nozzle;
a light irradiator for irradiating light on the measurement sample flowing through the flow cell;
a light receiver for receiving light given off from the material components in the measurement sample irradiated by light;
wherein the analyzing part analyzes characteristics parameters of the light received by the light receiver.

* * * * *